(12) United States Patent
    Tung

(10) Patent No.: US 9,181,190 B2
(45) Date of Patent: Nov. 10, 2015

(54) DEUTERATED VERCIRNON

(71) Applicant: Concert Pharmaceuticals Inc., Lexington, MA (US)

(72) Inventor: Roger D. Tung, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 14/412,169

(22) PCT Filed: Jul. 3, 2013

(86) PCT No.: PCT/US2013/049357
    § 371 (c)(1),
    (2) Date: Dec. 30, 2014

(87) PCT Pub. No.: WO2014/008417
    PCT Pub. Date: Jan. 9, 2014

(65) Prior Publication Data
    US 2015/0175546 A1    Jun. 25, 2015

Related U.S. Application Data

(60) Provisional application No. 61/668,019, filed on Jul. 4, 2012.

(51) Int. Cl.
    *C07D 213/89*    (2006.01)
    *A61K 31/44*     (2006.01)
    *C07B 59/00*     (2006.01)

(52) U.S. Cl.
    CPC ............. *C07D 213/89* (2013.01); *C07B 59/002* (2013.01); *C07B 2200/05* (2013.01)

(58) Field of Classification Search
    None
    See application file for complete search history.

(56) References Cited

U.S. PATENT DOCUMENTS

| | | | |
|---|---|---|---|
| 6,221,335 | B1 | 4/2001 | Foster |
| 6,440,710 | B1 | 8/2002 | Keinan et al. |
| 6,603,008 | B1 | 8/2003 | Ando et al. |
| 7,282,502 | B2 | 10/2007 | Fleming et al. |
| 7,420,055 | B2 | 9/2008 | Ungashe et al. |
| 7,517,990 | B2 | 4/2009 | Ito et al. |
| 7,932,252 | B2 | 4/2011 | Ungashe et al. |
| 8,211,896 | B2 | 7/2012 | Ungashe et al. |
| 2007/0082929 | A1 | 4/2007 | Gant et al. |
| 2007/0197695 | A1 | 8/2007 | Potyen et al. |
| 2008/0103122 | A1 | 5/2008 | Veltri |

FOREIGN PATENT DOCUMENTS

| WO | WO-95/26325 | A2 | 10/1995 |
|---|---|---|---|
| WO | WO-2007/118651 | A1 | 10/2007 |

OTHER PUBLICATIONS

Street et al, Journal of Chemical Research, Synopses (1987), (5), 154-5.*
International Search Report and Written Opinion of PCT/US2013/049357 dated Nov. 1, 2013.
D.J. Kushner et al; "Pharmacological Uses and Perspective of Heavy Water and Deuterated Compounds"; Can.J. Physiol. Pharmacol. 77, pp. 79-88(1999).
International Preliminary Report on Patentability and Written Opinion for PCT/US2013/049357 dated Jan. 6, 2015.
Baillie, T.A., "The Use of Stable Isotopes in Pharmacological Research," *Pharmacological Reviews*, 33(2): 81-138 (1981).
Browne, T. R., "Stable Isotope Techniques in Early Drug Develpment: An Economic Evaluation," *J. Clin. Pharmacol.*, 38: 213-220 (1998).
Cherrah, Y., et al., "Study of Deuterium Isotope Effects on Protein Binding by Gas Chromatography/Mass Spectrometry. Caffeine and Deuterated Isotopomers," *Biomedical and Environmental Mass Spectrometry*, 14: 653-657 (1987).
Dyck, L. E., et al., "Effects of Deuterium Substitution on the Catabolism of β-Phenylethylamine: An in Vivo Study," *Journal of Neurochemistry*, 46(2): 399-404 (1986).
Fisher, M.B. et al., "The Complexities Inherent in Attemps to Decrease Drug Clearance by Blocking Sites of CYP-Mediated Metabolism," *Curr. Opin. Drug Discov. Devel.*, 9(1):101-109 (2006).

(Continued)

*Primary Examiner* — Zinna Northington Davis
(74) *Attorney, Agent, or Firm* — Locke Lord LLP; Jeffrey D. Hsi

(57) ABSTRACT

The present invention in one embodiment provides a compound of Formula I:

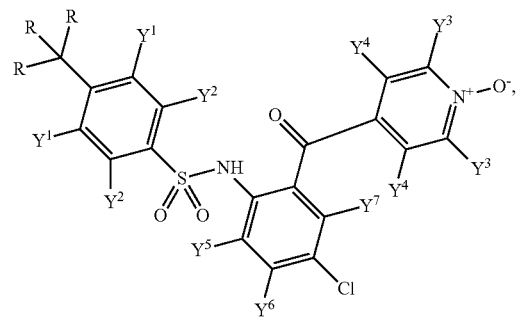

Formula I or a pharmaceutically acceptable salt thereof, wherein the variables shown in Formula I are as defined in the specification. The compound of Formula I is useful for the treatment of a disease selected from the group consisting of inflammatory bowel disease (IBD), such as Crohn's disease or ulcerative colitis, and celiac disease.

19 Claims, No Drawings

(56) References Cited

OTHER PUBLICATIONS

Foster, A. B., "Deuterium Isotope Effects in Studies of Drug Metabolism," *Trends in Pharmacological Sciences*, 5: 524-527 (1984).

Foster, A. B., "Deuterium Isotope Effects in the Metabolism of Drugs and Xenobiotics: Implications for Drug Design," *Advances in Drug Research*, 14: 1-40 (1985).

Fukuto, et al., Determination of the Mechanism of Demethylenation of (Methylenexioxy)phenyl Compounds by Cytochrome P450 Using Deuterium Isotope Effects, *J Med Chem*, 1991, 34:2871-2876.

Gouyette, A., "Synthesis of Deuterium-labelled Elliptinium and its Use in Metabolic Studies," *Biomedical and Environmental Mass Spectrometry*, 15: 243-247 (1988).

Haskins, N. J., "The Application of Stable Isotopes in Biomedical Research," *Biomedical Mass Spectrometry*, 9(7): 269-277 (1982).

Honma S., et al., "The Metabolism of Roxatidine Acetate Hydrochloride," *Drug Metabolism and Disposition*, 15(4): 551-559 (1987).

Pieniaszek, H. J., et al., "Moricizine Bioavailability via Simultaneous, Dual, Stable Isotope Administration: Bioequivalence Implications," *J. Clin. Pharmacol*, 39: 817-825 (1999).

Tonn, G. R., et al., "Simultaneous Analysis of Diphenyhydramine and a Stable Isotope Analog (2H10) Diphenhydramine Using Capillary Gas Chromatography with Mass Selective Detection in Biological Fluids from Chronically Instrumented Pregnant Ewes," *Biological Mass Spectrometry*, 22: 633-642 (1993).

Wolen, R. L., "The Application of Stable Isotopes to Studies of Drug Bioavailability and Bioequivalence," *J. Clin. Pharmacol.*, 26: 419-424 (1986).

\* cited by examiner

DEUTERATED VERCIRNON

RELATED APPLICATIONS

This application is the national phase under 35 U.S.C. §371 of PCT International Application No. PCT/US2013/049357, filed Jul. 3, 2013, which claims the benefit of and priority to U.S. Provisional Patent Application No. 61/668,019, filed Jul. 4, 2012, the contents of which are incorporated herein by reference.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:307-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

This invention relates to novel derivatives of vercirnon. This invention also provides compositions comprising a compound of this invention and the use of such compositions in methods of treating a disease or condition selected from the group consisting of inflammatory bowel disease (IBD), such as Crohn's disease or ulcerative colitis, and celiac disease, in a subject in need thereof.

Vercirnon is an inhibitor of CCR9 that is currently undergoing clinical development for the treatment of Crohn's disease (Phase III), ulcerative colitis and celiac disease (both in Phase II). According to Walters, M. J. et al., J Pharmacol. Exp. Ther. 2010, 335(1): 61, vercirnon controls the inappropriate immune system response underlying inflammatory bowel disease (IBD) by targeting the CCR9 chemokine receptor.

Despite the potential beneficial activities of vercirnon, there is a continuing need for new compounds to treat the aforementioned diseases and conditions.

DEFINITIONS

The term "treat" means decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of vercirnon will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically ex "D" or "deuterium", the position is understood to have deuterium at an abundance that is at least 3000 times greater than the natural abundance of deuterium, which is 0.015% (i.e., at least 45% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 55% of the compound. In other embodiments, the relative amount of such isotopologues in toto will be less than 50%, less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH~($C_1$-$C_6$)-alkylamine), such as N,N-dimethyl-N-(2-hydroxyethyl)amine or tri-(2-hydroxyethyl)amine; N-methyl D-glucamine; morpholine; thiomorpholine; piperidine; pyrrolidine; and amino acids such as arginine, lysine, and the like.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "$d_{x-y}$" refers to substitution with from x to y number of deuterium atoms. "Stereoisomer" refers to both enantiomers and diastereomers. "Tert" and "t-" each refer to tertiary. "US" refers to the United States of America.

"Substituted with deuterium" refers to the replacement of one or more hydrogen atoms with a corresponding number of deuterium atoms.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention in one embodiment provides a compound of Formula A:

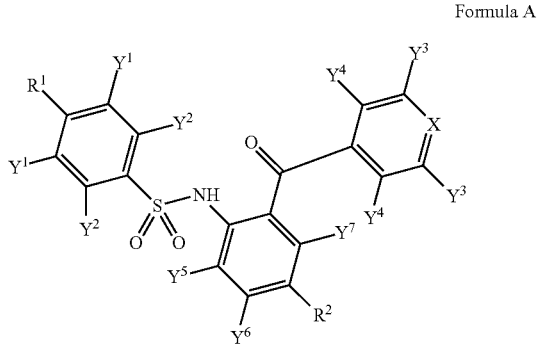

Formula A or a pharmaceutically acceptable salt thereof, wherein;
$R^1$ is selected from —OCH(CD$_3$)$_2$, OCD(CD$_3$)$_2$ and t-butyl optionally substituted with 1-9 deuterium;
$R^2$ is selected from —CD$_3$, —F and —Cl;
X is selected from N and N$_+$—O$^-$
each $Y^1$ is the same and is hydrogen or deuterium;
each $Y^2$ is the same and is hydrogen or deuterium;
each $Y^3$ is the same and is hydrogen or deuterium;
each $Y^4$ is the same and is hydrogen or deuterium;
$Y^5$ is hydrogen or deuterium;
$Y^6$ is hydrogen or deuterium; and
$Y^7$ is hydrogen or deuterium;
provided that if $R^1$ is C(CH$_3$)$_3$, $R^2$ is F or Cl, each $Y^1$ is hydrogen, each $Y^2$ is hydrogen, each $Y^3$ is hydrogen, each $Y^4$ is hydrogen, $Y^5$ is hydrogen, and $Y^6$ is hydrogen, then $Y^7$ is deuterium.

In one embodiment, the compound of Formula A is a compound of Formula I:

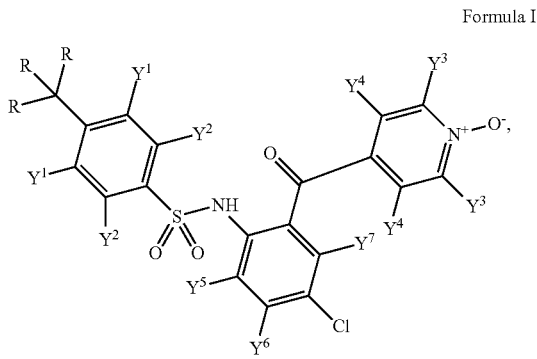

Formula I or a pharmaceutically acceptable salt thereof, wherein:
each R is the same and is CH$_3$, CDH$_2$, CHD$_2$, or CD$_3$;
each $Y^1$ is the same and is hydrogen or deuterium;
each $Y^2$ is the same and is hydrogen or deuterium;
each $Y^3$ is the same and is hydrogen or deuterium;
each $Y^4$ is the same and is hydrogen or deuterium;
$Y^5$ is hydrogen or deuterium;
$Y^6$ is hydrogen or deuterium; and
$Y^7$ is hydrogen or deuterium;
provided that if each R is CH$_3$, and each $Y^1$ is hydrogen, and each $Y^2$ is hydrogen, and each $Y^3$ is hydrogen, and each $Y^4$ is hydrogen, and $Y^5$ is hydrogen, and $Y^6$ is hydrogen, then $Y^7$ is deuterium.

In certain embodiments of the compound of Formula I, each R is CD$_3$. In one aspect of this embodiment, each $Y^1$ is hydrogen. In one example of this aspect, each $Y^2$ is hydrogen. In another example of this aspect, each $Y^2$ is deuterium. In one example of this aspect, each $Y^3$ is hydrogen. In another example of this aspect, each $Y^3$ is deuterium. In one example of this aspect, each $Y^4$ is hydrogen. In another example of this aspect, each $Y^4$ is deuterium.

In another aspect of the embodiment wherein each R is CD$_3$, each $Y^1$ is deuterium. In one example of this aspect, each $Y^2$ is hydrogen. In another example of this aspect, each $Y^2$ is deuterium. In one example of this aspect, each $Y^3$ is hydrogen. In another example of this aspect, each $Y^3$ is deuterium. In one example of this aspect, each $Y^4$ is hydrogen. In another example of this aspect, each $Y^4$ is deuterium.

In certain embodiments of the compound of Formula A or I, each Y is hydrogen. In one aspect of this embodiment, each $Y^2$ is hydrogen. In one example of this aspect, each $Y^3$ is hydrogen. In another example of this aspect, each $Y^3$ is deuterium. In one example of this aspect, each $Y^4$ is hydrogen. In another example of this aspect, each $Y^4$ is deuterium.

In another aspect of the embodiment wherein each $Y^1$ is hydrogen, each $Y^2$ is deuterium. In one example of this aspect, each $Y^3$ is hydrogen. In another example of this aspect, each $Y^3$ is deuterium. In one example of this aspect, each $Y^4$ is hydrogen. In another example of this aspect, each $Y^4$ is deuterium.

In one embodiment of the compound of Formula A or I, each $Y^2$ is hydrogen. In one aspect of this embodiment, each $Y^3$ is hydrogen. In one example of this aspect, each $Y^4$ is hydrogen. In another example of this aspect, each $Y^4$ is deuterium. In another aspect of the embodiment wherein each $Y^2$ is hydrogen, each $Y^3$ is deuterium. In one example of this aspect, each $Y^4$ is hydrogen. In another example of this aspect, each $Y^4$ is deuterium.

In one embodiment of the compound of Formula A or I, each $Y^3$ is hydrogen. In one aspect of this embodiment, each $Y^4$ is hydrogen. In another example of this aspect, each $Y^4$ is deuterium.

In one embodiment, the pharmaceutically acceptable salt is an alkali metal salt of the compound of Formula A or I, such as the sodium salt, shown below for formula

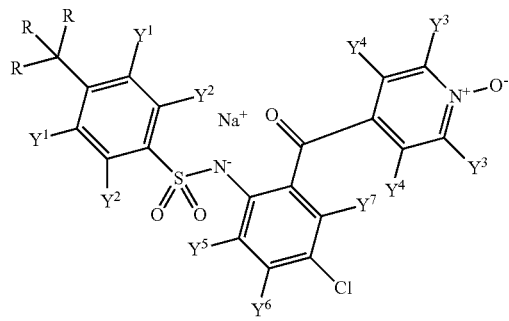

wherein each R, each $Y^1$, each $Y^2$, each $Y^3$, each $Y^4$, $Y^5$, $Y^6$ and $Y^7$ are as defined in any of the foregoing embodiments, aspects and/or examples.

In another set of embodiments, any atom not designated as deuterium in any of the embodiments, aspects, or examples set forth above is present at its natural isotopic abundance.

In yet another embodiment, a compound of Formula I is selected from any one of the compounds (Cmpd) set forth in Table 1 (below), wherein $Y^5$, $Y^6$ and $Y^7$ are each hydrogen:

| Cmpd # | each R | each $Y^1$ | each $Y^2$ | each $Y^3$ | each $Y^4$ |
|---|---|---|---|---|---|
| 100 | $CD_3$ | D | D | H | H |
| 101 | $CD_3$ | D | D | D | H |
| 102 | $CD_3$ | D | D | D | D |
| 103 | $CD_3$ | D | D | H | D |
| 104 | $CD_3$ | H | H | H | H |
| 105 | $CD_3$ | H | H | D | H |
| 106 | $CH_3$ | D | D | H | H |
| 107 | $CH_3$ | D | D | D | H |
| 108 | $CH_3$ | D | D | D | D |
| 109 | $CH_3$ | D | D | H | D |
| 111 | $CH_3$ | H | H | D | H |
| 112 | $CD_3$ | H | H | D | D |
| 113 | $CD_3$ | H | H | H | D |
| 114 | $CH_3$ | H | H | D | D |
| 115 | $CH_3$ | H | H | H | D | or a pharmaceutically acceptable salt thereof, wherein any atom not designated as deuterium is present at its natural isotopic abundance.

In another set of embodiments, any atom not designated as deuterium in any of the embodiments, aspects, or examples set forth above is present at its natural isotopic abundance.

The synthesis of compounds of Formula A or I may be readily achieved by synthetic chemists of ordinary skill by reference to the Exemplary Synthesis and Examples disclosed herein. Relevant procedures analogous to those of use for the preparation of compounds of Formula I and intermediates thereof are disclosed, for instance in U.S. Pat. No. 7,420,055 and US Patent Application No. 20060111351.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

Scheme 1 provides an exemplary procedure for the preparation of the compounds of Formula I wherein, by way of example only, each R is $CD_3$.

Scheme 1: A Method for the Preparation of Compounds of Formula I Wherein Each R is $CD_3$.

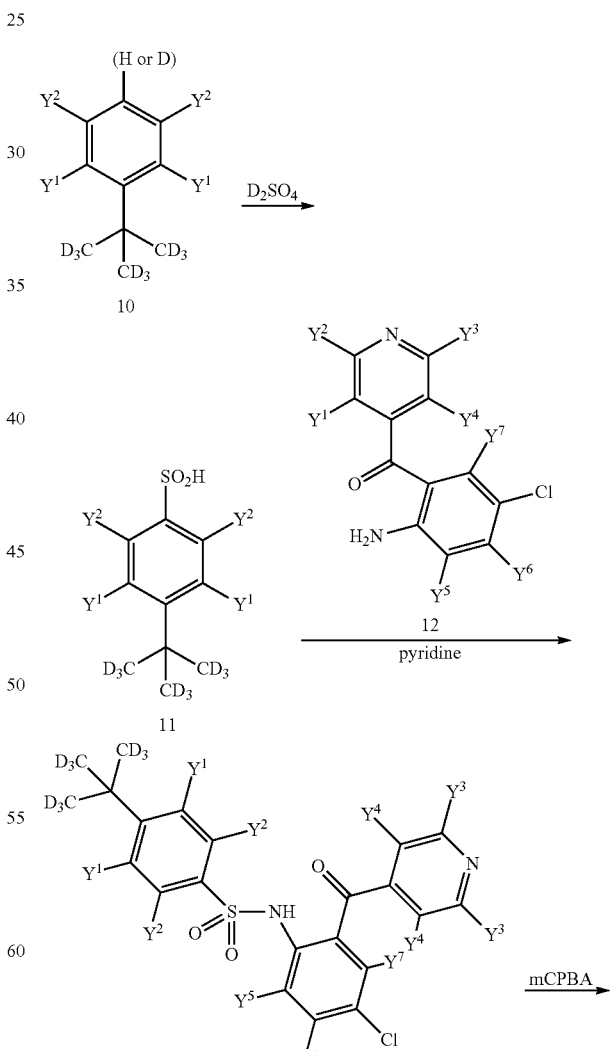

-continued

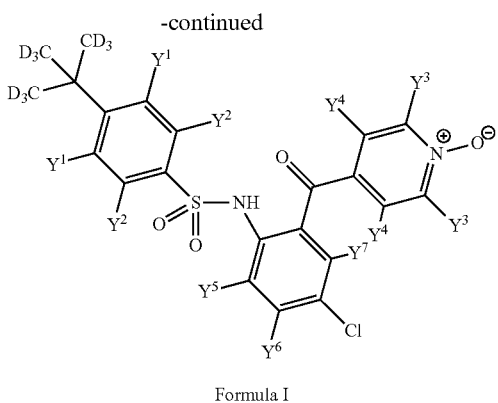

Formula I

The compounds of Formula I may be prepared in a manner analogous to the synthesis described in U.S. Pat. No. 7,420,055 ("the '055 patent") in columns 76 (from line 55) to 90 (to line 28), the contents of which are incorporated by reference herein. For example, as shown in Scheme 1 above, compound 10 is treated with $D_7SO_4$ to provide 11. Coupling of 11 with 12 yields 13, which is oxidized by mCPBA to give a compound of Formula I wherein each R is $CD_3$.

Examples of intermediates that may be used in accordance with Scheme 1 include 10a, 10b, and 12a, shown below. 10a and 12a are commercially available, and 10b may be synthesized as described in US20100063076.

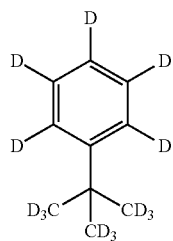

10a

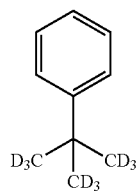

10b

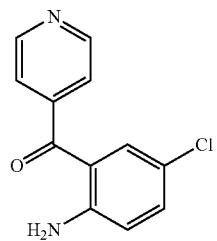

12a

Thus, for example, 10a may be used as the starting material in Scheme 1 to ultimately provide a compound of Formula I wherein each $Y^1$ is deuterium and each $Y^2$ is deuterium, while 10b may be used as the starting material in Scheme 1 to ultimately provide a compound of Formula I wherein each $Y^1$ is hydrogen and each $Y^2$ is hydrogen. As another example, compound 12a may be used as an intermediate in Scheme 1 to ultimately provide a compound of Formula I wherein each $Y^3$ is hydrogen, each $Y^4$ is hydrogen, $Y^5$ is hydrogen, $Y^6$ is hydrogen, and $Y^7$ is hydrogen.

The specific approaches and compounds above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $Y^1$, $Y^2$, $Y^3$, etc.) or not. The suitability of a chemical group in a compound structure for use in the synthesis of another compound is within the knowledge of one of ordinary skill in the art.

Additional methods of synthesizing compounds of Formula A or I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene, T W et al., *Protective Groups in Organic Synthesis*, 3$^{rd}$ Ed., John Wiley and Sons (1999); Fieser, L et al., *Fieser and Fieser's Reagents for Organic Synthesis*, John Wiley and Sons (1994); and Paquette, L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pharmaceutical compositions comprising an effective amount of a compound of Formula A or I (e.g., including any of the formulae herein), or a pharmaceutically acceptable salt of said compound; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the subject, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as vercirnon. Such agents include those indicated as being useful in combination with vercirnon, including but not limited to, those described in U.S. Pat. No. 7,420,055 and US Patent Application No. 20060111351.

Preferably, the second therapeutic agent is an agent useful in the treatment of a disease of condition selected from the group consisting of inflamatory bowel disease (IBD), such as Crohn's disease or ulcerative colitis, and celiac disease.

In another embodiment, the invention provides separate dosage forms of a compound of fins invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this invention can range from 10 mg to 1000 mg, such as 50 mg to 500 mg, such as 100 mg to 250 mg. For example, 10 mg to 1000 mg, such as 50 mg to 500 mg, such as 100 mg to 250 mg, may be administered once a day. Alternatively, 5 mg to 500 mg, such as 25 mg to 250 mg, such as 50 mg to 125 mg, may be administered twice a day.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of inhibiting the activity of CCR9 in a cell, comprising contacting a cell with one or more compounds of Formula A or I herein.

According to another embodiment, the invention provides a method of treating a disease or condition selected from the group including allergic diseases such as systemic anaphylaxis or hypersensitivity responses, drug allergies, insect sting allergies, and food allergies; inflammatory bowel diseases, such as Crohn's disease, ulcerative colitis, ileitis and enteritis;

vaginitis; psoriasis and inflammatory dermatoses such as dermatitis, eczema, atopic dermatitis, allergic contact dermatitis, urticaria and pruritus; vasculitis; spondyloarthropathies; scleroderma; asthma and respiratory allergic diseases such as allergic asthma, allergic rhinitis and hypersensitivity lung diseases; autoimmune diseases, such as fibromyalgia, scleroderma, ankylosing spondylitis, juvenile rheumatoid arthritis (RA), Still's disease, polyarticular juvenile RA, pauciarticular juvenile RA, polymyalgia rheumatica, rheumatoid arthritis, psoriatic arthritis, osteoarthritis, polyarticular arthritis, multiple sclerosis, systemic lupus erythematosus, type I diabetes, type II diabetes, glomerulonephritis; graft rejection, including allograft rejection; atherosclerosis, myositis, neurodegenerative diseases (for example, Alzheimer's disease) encephalitis, meningitis, hepatitis, nephritis, sepsis, sarcoidosis, allergic conjunctivitis, otitis, chronic obstructive pulmonary disease, sinusitis, Behcet's syndrome and gout; immune mediated food allergies such as Coeliac (Celiac) disease; pulmonary fibrosis and other fibrotic diseases; and irritable bowel syndrome.

According to another embodiment, the invention provides a method of treating a disease or condition selected from the group consisting of inflammatory bowel disease (IBD), such as Crohn's disease or ulcerative colitis, and celiac disease, in a subject in need thereof, comprising the step of administering to the subject an effective amount of a compound or a composition of this invention.

Identifying a subject in need of such treatment can be in the judgment of a subject or a health care professional and can be subjective (e.g. opinion) or objective (e.g. measurable by a test or diagnostic method). In one embodiment the subject is a patient.

In another embodiment, any of the above methods of treatment comprises the further step of co-administering to the subject in need thereof one or more second therapeutic agents. The choice of second therapeutic agent may be made from any second therapeutic agent known to be useful for co-administration with vercirnon. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In one embodiment, the method of treating Crohn's disease in a subject with a compound or composition of this invention comprises the additional step of co-administering to the subject in need thereof a second agent suitable for treating Crohn's disease.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn., (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized Other potential advantages (including without limitation improved dosing regimens and/or reduced drug cost) will be apparent to those of skill in the art.

In yet another aspect, the invention provides the use of a compound of Formula A or I alone or together with one or more of the above-described second therapeutic agents in the manufacture of a medicament, either as a single composition or as separate dosage forms, for treatment in a subject of a disease, disorder or symptom set forth above. Another aspect of the invention is a compound of Formula for use in the treatment in a subject of a disease, disorder or symptom thereof delineated herein.

EXAMPLE 1

Evaluation of Metabolic Stability

Microsomal Assay:
Human liver microsomes (20 mg/mL) are obtained from Xenotech, LLC (Lenexa, Kans.). β-nicotinamide adenine dinucleotide phosphate, reduced form (NADPH), magnesium chloride ($MgCl_2$), and dimethyl sulfoxide (DMSO) are purchased from Sigma-Aldrich.

Determination of Metabolic Stability:
7.5 mM stock solutions of test compounds are prepared in DMSO. The 7.5 mM stock solutions are diluted to 12.5-50 µM in acetonitrile (ACN). The 20 mg/mL human liver microsomes are diluted to 0.625 mg/mL in 0.1 M potassium phosphate buffer, pH 7.4, containing 3 mM $MgCl_2$. The diluted microsomes are added to wells of a 96-well deep-well polypropylene plate in triplicate. A 10 µL aliquot of the 12.5-50 µM test compound is added to the microsomes and the mixture is pre-warmed for 10 minutes. Reactions are initiated by addition of pre-warmed NADPH solution. The final reaction volume is 0.5 mL and contains 0.5 mg/mL human liver microsomes, 0.25-1.0 µM test compound, and 2 mM NADPH in 0.1 M potassium phosphate buffer, pH 7.4, and 3 mM $MgCl_2$. The reaction mixtures are incubated at 37° C., and 50 µL aliquots are removed at 0, 5, 10, 20, and 30 minutes and added to shallow-well 96-well plates which contain 50 L of ice-cold ACN with internal standard to stop the reactions. The plates are stored at 4° C. for 20 minutes after which 100 µL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. The same procedure is followed for the non-deuterated counterpart of the compound of Formula I and the positive control, 7-ethoxycoumarin (1 μM). Testing is done in triplicate.

Data Analysis:

The in vitro $t_{1/2}$s for test compounds are calculated from the slopes of the linear regression of % parent remaining (ln) vs incubation time relationship.

in vitro $t_{1/2}$=0.693/k k=−[slope of linear regression of % parent remaining (ln)vs incubation time]

Data analysis is performed using Microsoft Excel Software.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

I claim:

1. A compound of Formula I:

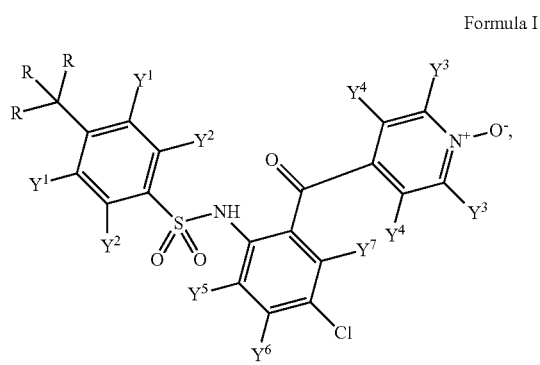

Formula I or a pharmaceutically acceptable salt thereof, wherein:

each R is the same and is $CH_3$, $CDH_2$, $CHD_2$, or $CD_3$;

each $Y^1$ is the same and is hydrogen or deuterium;

each $Y^2$ is the same and is hydrogen or deuterium;

each $Y^3$ is the same and is hydrogen or deuterium;

each $Y^4$ is the same and is hydrogen or deuterium;

$Y^5$ is hydrogen or deuterium;

$Y^6$ is hydrogen or deuterium; and $Y^7$ is hydrogen or deuterium;

provided that if each R is $CH_3$, and each $Y^1$ is hydrogen, and each $Y^2$ is hydrogen, and each $Y^3$ is hydrogen, and each $Y^4$ is hydrogen, and $Y^5$ is hydrogen, and $Y^6$ is hydrogen, then $Y^7$ is deuterium.

2. The compound of claim 1, wherein the compound is an alkali metal salt of the compound of Formula I.

3. The compound of claim 2, wherein the compound is

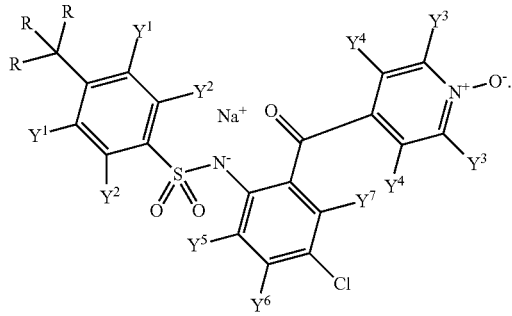

4. The compound of claim 1, wherein each R is $CD_3$.
5. The compound of claim 1, wherein each $Y^1$ is hydrogen.
6. The compound of claim 1, wherein each $Y^1$ is deuterium.
7. The compound of claim 1, wherein each $Y^2$ is hydrogen.
8. The compound of claim 1, wherein each $Y^2$ is deuterium.
9. The compound of claim 1, wherein each $Y^3$ is hydrogen.
10. The compound of claim 1, wherein each $Y^3$ is deuterium.
11. The compound of claim 1, wherein each $Y^4$ is hydrogen.
12. The compound of claim 1, wherein each $Y^4$ is deuterium.
13. The compound of claim 1, wherein the compound is selected from any one of the compounds (Cmpd) set forth in the table below, wherein $Y^5$, $Y^6$ and $Y^7$ are each hydrogen:

| Cmpd # | each R | each $Y^1$ | each $Y^2$ | each $Y^3$ | each $Y^4$ |
|---|---|---|---|---|---|
| 100 | $CD_3$ | D | D | H | H |
| 101 | $CD_3$ | D | D | D | H |
| 102 | $CD_3$ | D | D | D | D |
| 103 | $CD_3$ | D | D | H | D |
| 104 | $CD_3$ | H | H | H | H |
| 105 | $CD_3$ | H | H | D | H |
| 106 | $CH_3$ | D | D | H | H |
| 107 | $CH_3$ | D | D | D | H |
| 108 | $CH_3$ | D | D | D | D |
| 109 | $CH_3$ | D | D | H | D |
| 111 | $CH_3$ | H | H | D | H |
| 112 | $CD_3$ | H | H | D | D |
| 113 | $CD_3$ | H | H | H | D |
| 114 | $CH_3$ | H | H | D | D |
| 115 | $CH_3$ | H | H | H | D | or a pharmaceutically acceptable salt thereof, wherein any atom not designated as deuterium is present at its natural isotopic abundance.

14. The compound of claim 1, wherein any atom not designated as deuterium is present at its natural isotopic abundance.

15. A pharmaceutical composition comprising a compound of claim 1 or a pharmaceutically acceptable salt thereof; and a pharmaceutically acceptable carrier.

16. A method of treating a disease selected from the group consisting of IBD and celiac disease in a subject, comprising administering to the subject in need thereof a pharmaceutical composition of claim 15.

17. The method of claim 16, wherein the disease is IBD.

18. The method of claim 17, wherein the disease is Crohn's disease.

19. The method of claim 17, wherein the disease is ulcerative colitis.

* * * * *